US012636157B2

(12) United States Patent
Curtis et al.

(10) Patent No.: US 12,636,157 B2
(45) Date of Patent: May 26, 2026

(54) ADDITIVE MANUFACTURING ON MACHINED ASSEMBLED PARTS

(71) Applicant: Howmedica Osteonics Corp., Mahwah, NJ (US)

(72) Inventors: Michael Curtis, Kildare (IE); Collin Newman, Wayne, NJ (US); John Teahan, Cork (IE); Christopher S. Bobish, Middletown, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 19/275,040

(22) Filed: Jul. 21, 2025

(65) Prior Publication Data

US 2026/0020963 A1      Jan. 22, 2026

Related U.S. Application Data

(60) Provisional application No. 63/673,975, filed on Jul. 22, 2024.

(51) Int. Cl.
| | |
|---|---|
| *A61F 2/30* | (2006.01) |
| *A61F 2/44* | (2006.01) |
| *B33Y 10/00* | (2015.01) |
| A61B 17/00 | (2006.01) |
| B33Y 40/20 | (2020.01) |
| B33Y 80/00 | (2015.01) |

(52) U.S. Cl.
CPC .......... *A61F 2/3094* (2013.01); *A61F 2/4455* (2013.01); *B33Y 10/00* (2014.12); *A61B 2017/00526* (2013.01); *A61F 2002/30985* (2013.01); *B33Y 40/20* (2020.01); *B33Y 80/00* (2014.12)

(58) Field of Classification Search
CPC ......... A61B 2017/00526; A61F 2/3094; A61F 2002/30985; A61F 2/4455; A61F 2240/00; B33Y 10/00; B33Y 80/00
See application file for complete search history.

(56) References Cited

U.S. PATENT DOCUMENTS

| | | |
|---|---|---|
| 8,888,480 B2 | 11/2014 | Yoo et al. |
| 9,321,215 B2 | 4/2016 | Dudley |

(Continued)

FOREIGN PATENT DOCUMENTS

| | | |
|---|---|---|
| EP | 3338918 A1 | 6/2018 |
| WO | 2012076205 A1 | 6/2012 |

*Primary Examiner* — Larry E Waggle, Jr.
(74) *Attorney, Agent, or Firm* — Lerner David LLP

(57) ABSTRACT

An implant having two adjacent solid parts, a third solid part disposed between the two solid parts, and a porous part extending from the solid parts. The implant is fabricated by a process that includes first assembling the solid parts before additively manufacturing the porous part on surfaces defined by the solid parts. This process may include positioning a first fabricated component adjacent to a second fabricated component such that a side surface of the first fabricated component and a side surface of the second fabricated component form a build surface. Then additively manufacturing a structure on the build surface such that the structure extends across and is permanently fixed to both of the side surfaces of the first and the second fabricated components such that the first and the second fabricated components form part of the implant.

20 Claims, 7 Drawing Sheets

(56)            References Cited

U.S. PATENT DOCUMENTS

|  |  |  |  |  |
|---|---|---|---|---|
| 9,679,085 | B2 | 6/2017 | Cudak et al. | |
| 9,993,873 | B2 | 6/2018 | Kovalcik et al. | |
| 10,307,194 | B2 * | 6/2019 | Tempco | B29C 64/245 |
| 10,717,238 | B2 | 7/2020 | Kessling et al. | |
| 10,821,668 | B2 | 11/2020 | Thompson | |
| 11,712,277 | B2 | 8/2023 | Tempco et al. | |
| 12,151,310 | B2 * | 11/2024 | Tempco | B33Y 80/00 |
| 2008/0006966 | A1 | 1/2008 | Mannella | |
| 2009/0177309 | A1 | 7/2009 | Kozlak | |
| 2013/0108726 | A1 | 5/2013 | Uckelmann et al. | |
| 2017/0173892 | A1 | 6/2017 | Steele | |
| 2020/0164439 | A1 * | 5/2020 | Tsai | A61F 2/3094 |
| 2020/0238615 | A1 | 7/2020 | Staal et al. | |
| 2022/0324159 | A1 | 10/2022 | Natale et al. | |
| 2023/0211555 | A1 | 7/2023 | Rodriguez Santiago et al. | |
| 2023/0286219 | A1 * | 9/2023 | Zaugg | B33Y 40/20 |
| 2025/0099263 | A1 * | 3/2025 | Seaman | A61F 2/4455 |
| 2025/0205060 | A1 * | 6/2025 | Phillips | A61F 2/4455 |

* cited by examiner

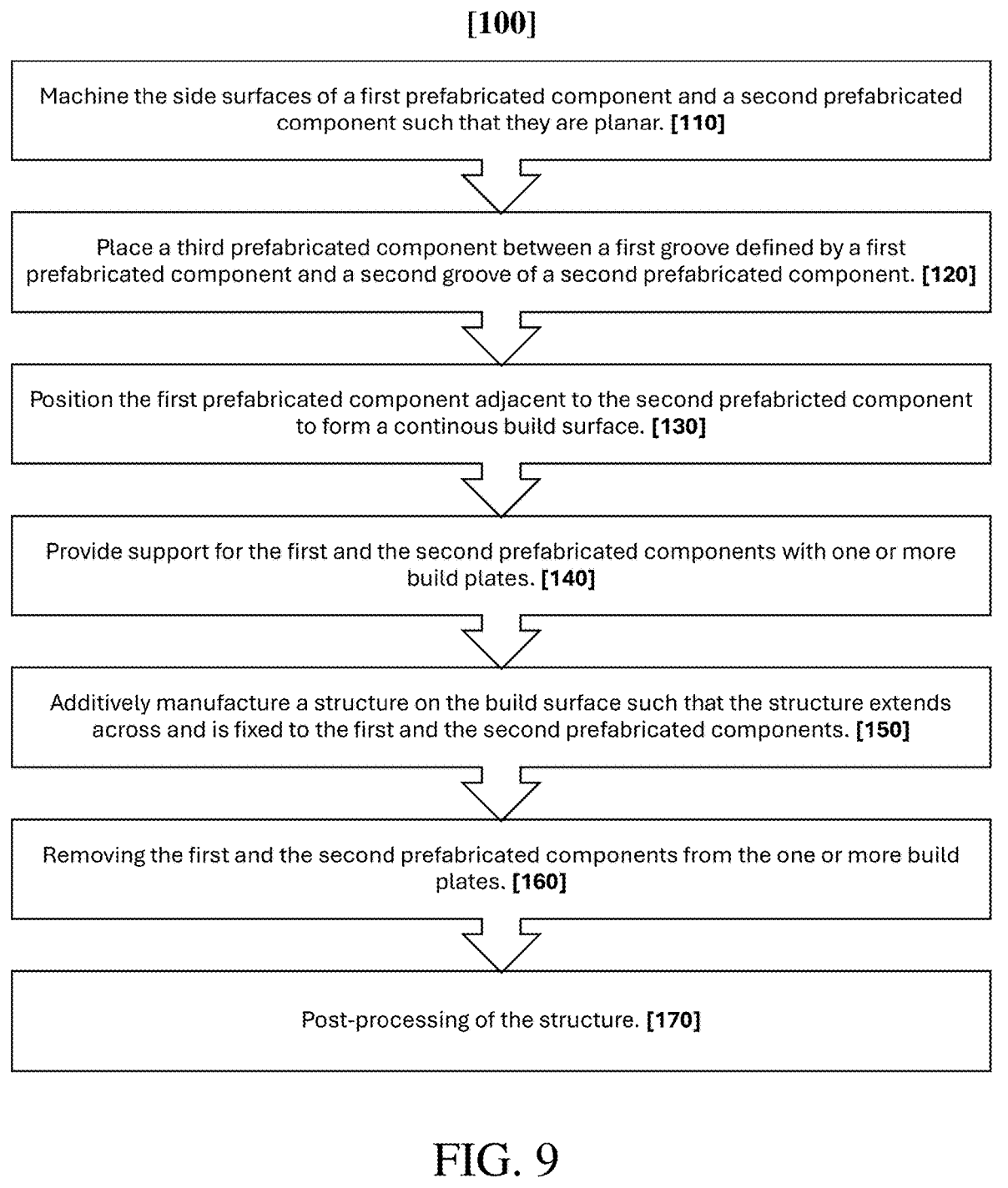

[100]

Machine the side surfaces of a first prefabricated component and a second prefabricated component such that they are planar. [110]

Place a third prefabricated component between a first groove defined by a first prefabricated component and a second groove of a second prefabricated component. [120]

Position the first prefabricated component adjacent to the second prefabricted component to form a continous build surface. [130]

Provide support for the first and the second prefabricated components with one or more build plates. [140]

Additively manufacture a structure on the build surface such that the structure extends across and is fixed to the first and the second prefabricated components. [150]

Removing the first and the second prefabricated components from the one or more build plates. [160]

Post-processing of the structure. [170]

FIG. 9

ADDITIVE MANUFACTURING ON MACHINED ASSEMBLED PARTS

CROSS-REFERENCE TO RELATED APPLICATIONS

This application claims the benefit of the filing date of U.S. Provisional Patent Application No. 63/673,975 filed Jul. 22, 2024, the disclosure of which is hereby incorporated herein by reference in its entirety.

BACKGROUND

In the medical field, additive manufacturing has allowed for significant advancements in novel structural features for and customization of implants and prosthetics to better fit the needs of patients. For example, additive manufacturing is particularly apt for fabricating porous implants that facilitate bone ingrowth. While such advantages may make additive manufacturing highly attractive, additive manufacturing has certain drawbacks when compared to subtractive manufacturing techniques. For example, the surface quality of parts additively manufactured is often not as refined as that achieved by subtractive manufacturing, which can greatly impact part assemblies when interconnecting surface features lack quality and precision. While additive manufacturing is capable of fabricating parts with high precision, this often requires a lot of time compared to subtractive manufacturing processes, which makes subtractive manufacturing a great option when certain components require such features.

As such, there remains a need for part designs and manufacturing methods that utilize the advantages of both additive and subtractive manufacturing.

BRIEF SUMMARY

The specific arrangements disclosed herein relate to an implant that comprises a first portion fabricated through subtractive manufacturing and a second portion fabricated through additive manufacturing in a way that leverages the advantages of these two manufacturing techniques. The first portion includes a first part, a second part and a third part, the third part is rotatably disposed and secured between the first and the second parts. The first part and the second part are positioned adjacent to each other such that they form a build surface that extends across side surfaces of the first and the second part. The first, second, and third parts are prefabricated through subtractive manufacturing, e.g., a machining process, and assembled before the second portion is formed.

Once the first portion of the implant is fabricated and assembled, the first few layers of the second portion are additively manufactured (i.e., 3D printed) across the entire width and length of the build surface defined by the first and the second parts. These first few layers of the second portion are fused to the first and the second parts and thereby bind the first and the second parts together. After the first few layers of the second portion are formed, subsequent layers are added to form a porous structure that extends away from the first portion. The porous structure can be customized as to its shape, size, porosity, etc. In this manner, the implant utilizes the precision of subtractive manufacturing and the porous structures created by additive manufacturing.

According to an aspect of the disclosure, an implant may be assembled by a process. In the process, a first fabricated component may be positioned adjacent to a second component such that a side surface of the first fabricated component and a side surface of the second fabricated component together form a build surface. Then a structure may be additively manufactured on the build surface such that the structure extends across and is fixed to both of the side surfaces of the first and the second fabricated components. In such instances, the first and the second fabricated components may be integral with the implant and fused together via the structure. In other instances, side surfaces of the first and the second fabricated components may be machined such that the build surface is planar. The first and the second fabricated components may be fabricated via subtractive manufacturing. The structure may cover the entire build surface.

In yet other arrangements, respective grooves of the first and the second fabricated components may be positioned to form a cavity. In such instances, a third fabricated component may be placed between the grooves of the first and the second fabricated components such that the positioning step at least partly disposes the third fabricated component within the cavity. The build surface may lie between the third fabricated component and the structure. In some instances, the additively manufacturing step may fix the relative positions of the first and the second fabricated components such that the third fabricated component is held in place at least partially within the cavity upon completion of the additively manufacturing step. The third fabricated component may be movable relative to the first and the second fabricated components upon completion of the additively manufacturing step. The third fabricated component is pivotable and/or rotatable relative to the first and the second fabricated components upon completion of the additively manufacturing step. The structure may be porous and the build surface may be solid.

In some arrangements, the process may include a step of post-processing the implant. The post-processing step may include polishing a portion of the implant. The structure may be integral with the first and the second fabricated components. The first and the second fabricated components are supported with one or more build plates. The first and the second fabricated components may be supported by a top surface of the one or more build plates. The first and the second fabricated components may be supported by a surface of the one or more build plates beneath a top surface of the one or more build plates. At least one of the first and the second fabricated components may be prefabricated. The first and the second fabricated components may be removed from the one or more build plates. The build surface may be a continuous surface.

According to another aspect of the disclosure, an implant may include a first solid part, a second solid part that may be adjacent to the first solid part, a porous portion extending from the first and the second solid parts, and a third solid part disposed between the first and the second solid parts. The porous part may secure (e.g., fuse) the first solid part and the second solid together. The porous part may be additively manufactured. The porous part may be integral with the first and the second solid parts. The first solid part may include a first surface, and the second solid part may include a second surface adjacent to the first surface such that the porous part extends from the first and the second surfaces. The first and the second surfaces may be machined surfaces. The third solid part may be movable relative to the first and the second solid parts. The third solid part may be pivotable relative to the first and the second solid parts. Both the first and the second solid parts may include respective grooves between which the third solid part is positioned.

BRIEF DESCRIPTION OF THE DRAWINGS

A more complete appreciation of the subject matter of the present disclosure and the various advantages thereof may be realized by reference to the following detailed description which refers to the accompanying drawings, in which:

FIG. 9 is a process flow diagram outlining an implant assembly and fabrication in accordance with an aspect of the present disclosure.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. The term "step of" does not mean "step for."

Figure 1:
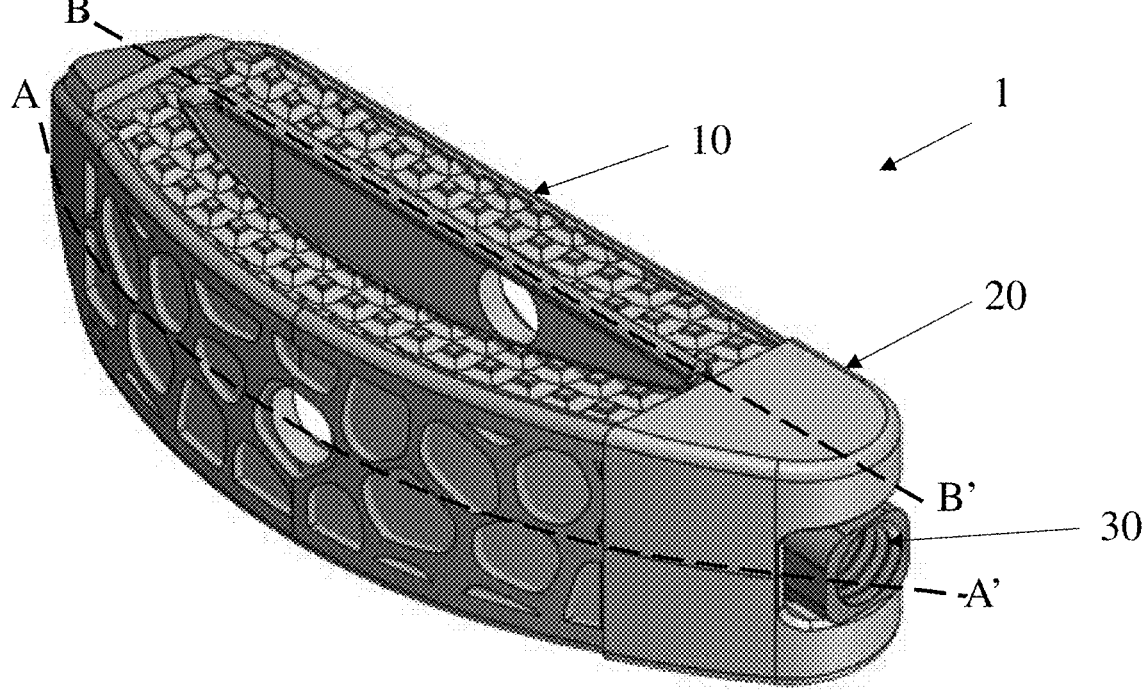
FIG. 1 is a perspective view of an implant in accordance with an aspect of the present disclosure.
Figure 4:
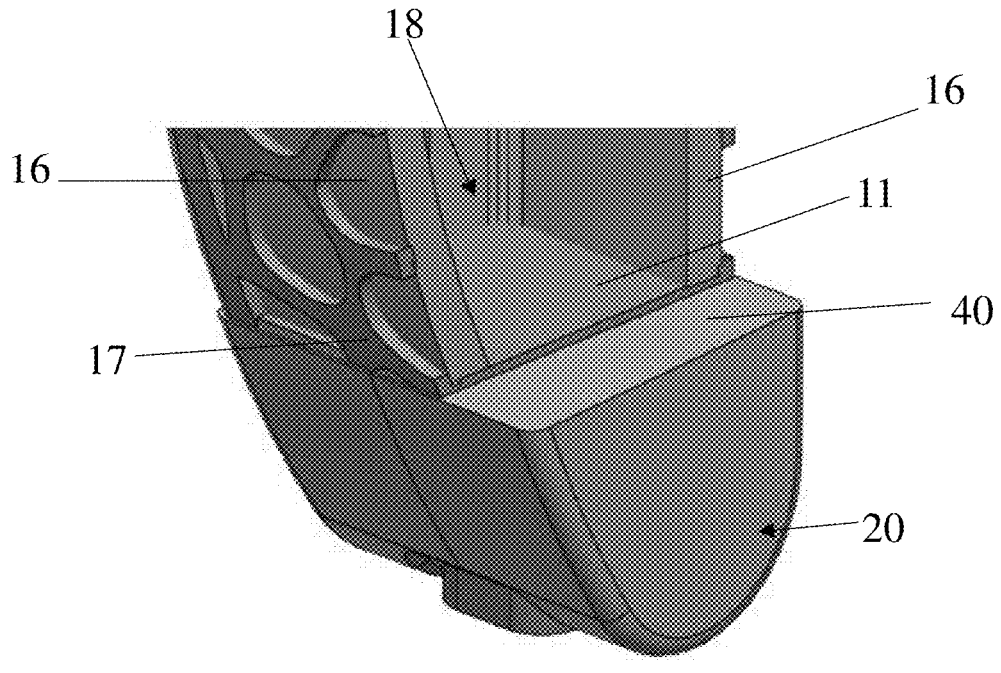
FIG. 4 is a partial perspective view of the implant shown in FIG. 3B.
Figure 5:
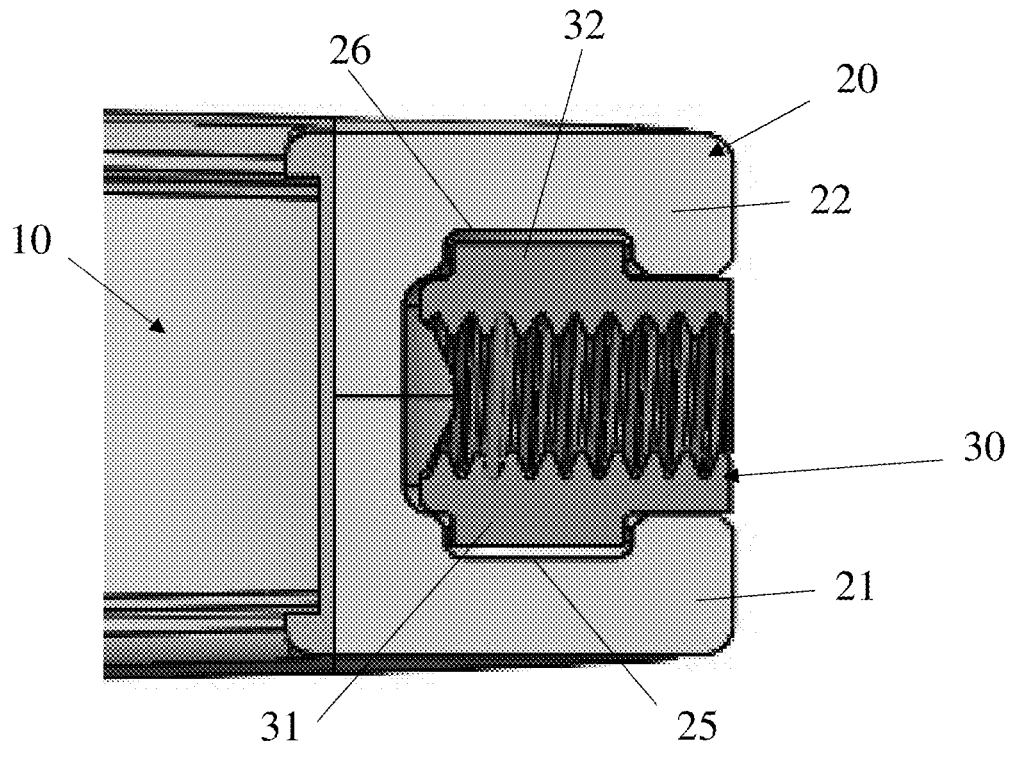
FIG. 5 is a cross-sectional view of the implant shown in FIG. 1 across B-B'.
Figure 6:
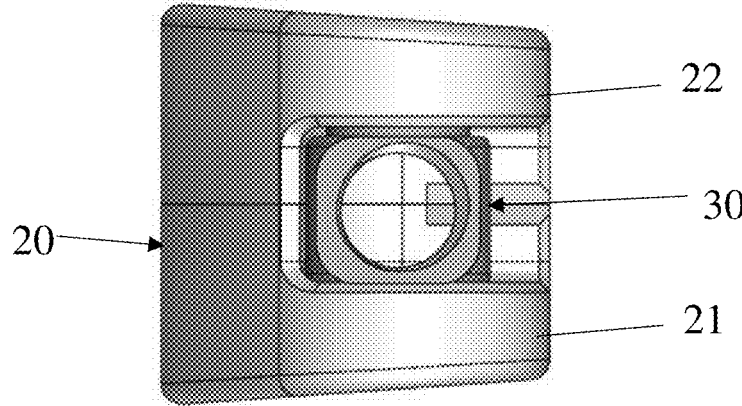
FIG. 6 is a bottom view of a part assembly of the implant of FIG. 1.
Figure 7:
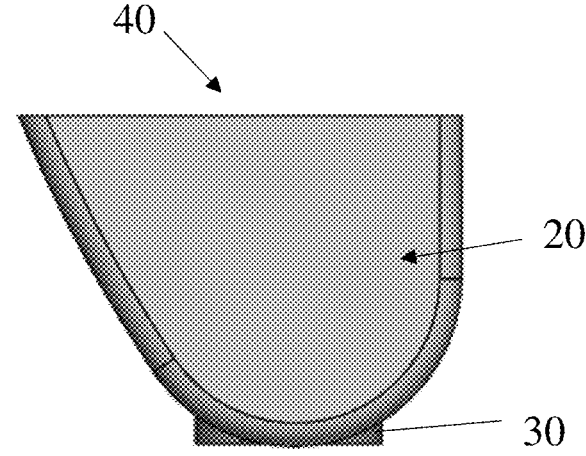
FIG. 7 is a side view of the part assembly of FIG. 6.
Figure 8:
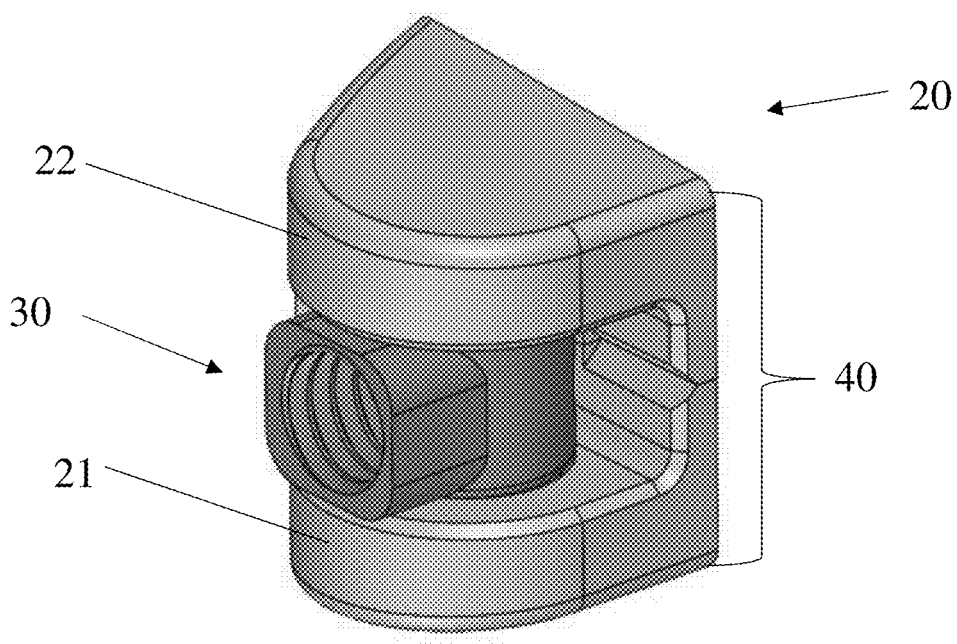
FIG. 8 is a perspective view of the part assembly of FIG. 6.

Referring now to the drawings, FIGS. 1-8 illustrate an implant 1 that has a porous portion 10, a solid portion 20, and a rotatable portion 30. Solid portion 20 includes a first solid part 21 and a second solid part 22 that are positioned adjacent to each other such that a first side surface 23 of the first solid part and a second side surface 24 of the second solid part together form a build surface 40 that is planar and continuous, as best shown in FIGS. 6-8. Porous portion 10 is attached to (e.g., fused) and extends from build surface 40 such that the porous portion securely holds the first and the second solid parts in a permanently fixed configuration, as shown in FIG. 1. Generally, first side surface 23 and second side surface 24 are machined surfaces to ensure they fit uniformly together to form one continuous planar surface (discussed in more detail below).

First solid part 21 includes a first cavity 25 that corresponds to a second cavity 26 defined by second solid part 22 such that the first cavity and the second cavity align when the first and the second solid parts are assembled, and the first cavity and the second cavity have the same shape and dimensions. A first sidewall 27 extends around a portion of first cavity 25, and a second sidewall 28 extends around a portion of second cavity 26 such that the first and the second sidewalls also align when first solid part 21 and second solid part 22 are assembled. First sidewall 27 is spaced apart from the outer edge of first cavity 25, and second sidewall 28 is similarly spaced apart from the outer edge of second cavity 26, as shown in FIG. 5. Solid portion 20 further includes an interlocking feature such that first solid part 21 has a protrusion 29 extending from the first solid part, and second solid part 22 has a slot (not shown) configured to receive the protrusion. In this manner, the first and the second solid parts interlock when assembled to prevent movement between the two parts before and during the formation of porous portion 10 (discussed in more detail below).

Still referring to FIGS. 1-8, rotatable portion 30 includes a first extension 31, a second extension 32, and a shaft 33 that defines a hole 34 extending along the longitudinal axis of the shaft. Hole 34 of shaft 33 is threaded such that an insertion tool can be engaged therein to facilitate the implantation of implant 1. First extension 31 and second extension 32 both have a tubular shape and have a circumference smaller than that of first cavity 25 and second cavity 26, as shown in FIG. 5, and the first and the second extensions extend from rotatable portion 30 in opposite directions along a first axis 36 that is perpendicular to the central axis 37 of shaft 33. Rotatable portion 30 further includes an enlarged tubular region 35 positioned between first extension 31 and second extension 32. Rotatable portion 30 is disposed between first solid part 21 and second solid part 22 such that first extension 31 is positioned within first cavity 25 of the first solid part and second extension 32 is positioned within second cavity 26 of the second solid part such that the rotatable portion can rotate freely between the first and the second solid parts. For example, shaft 33 of rotatable portion 30 is configured to rotate at least 90 degrees when the solid portion 20 and the rotatable portion are assembled together. For certain surgical techniques and procedures, like transforaminal lumbar interbody fusion (TLIF) used for spinal fusion, shaft 33 may be configured to rotate over 90 degrees to facilitate the approach for implanting of the implant. In this manner, shaft 33 can pivot about the first axis to allow hole 34 to be aligned with and threaded onto an insertion tool.

Figure 2:
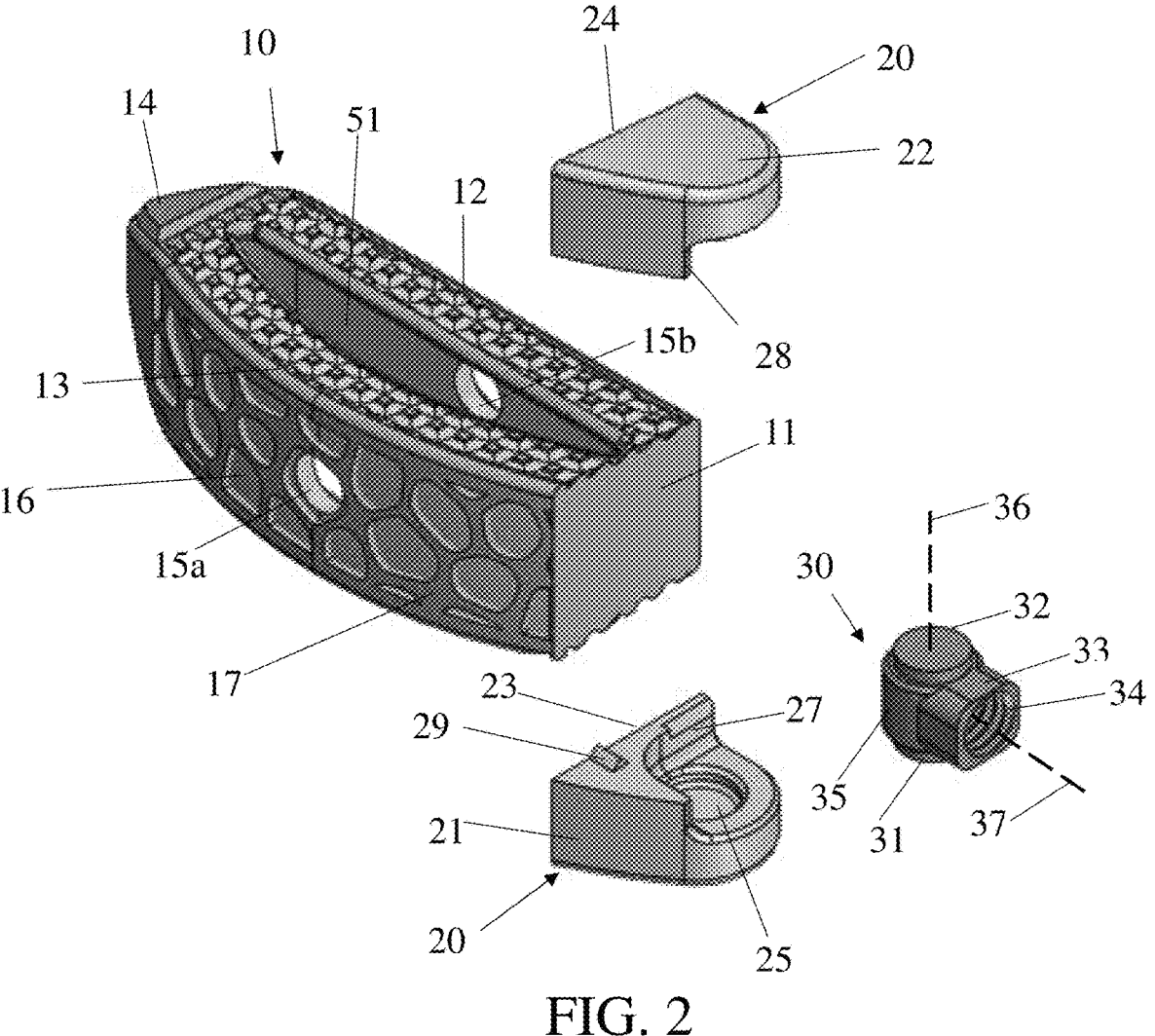
FIG. 2 is an exploded view of the implant shown in FIG. 1.
Figure 3A:
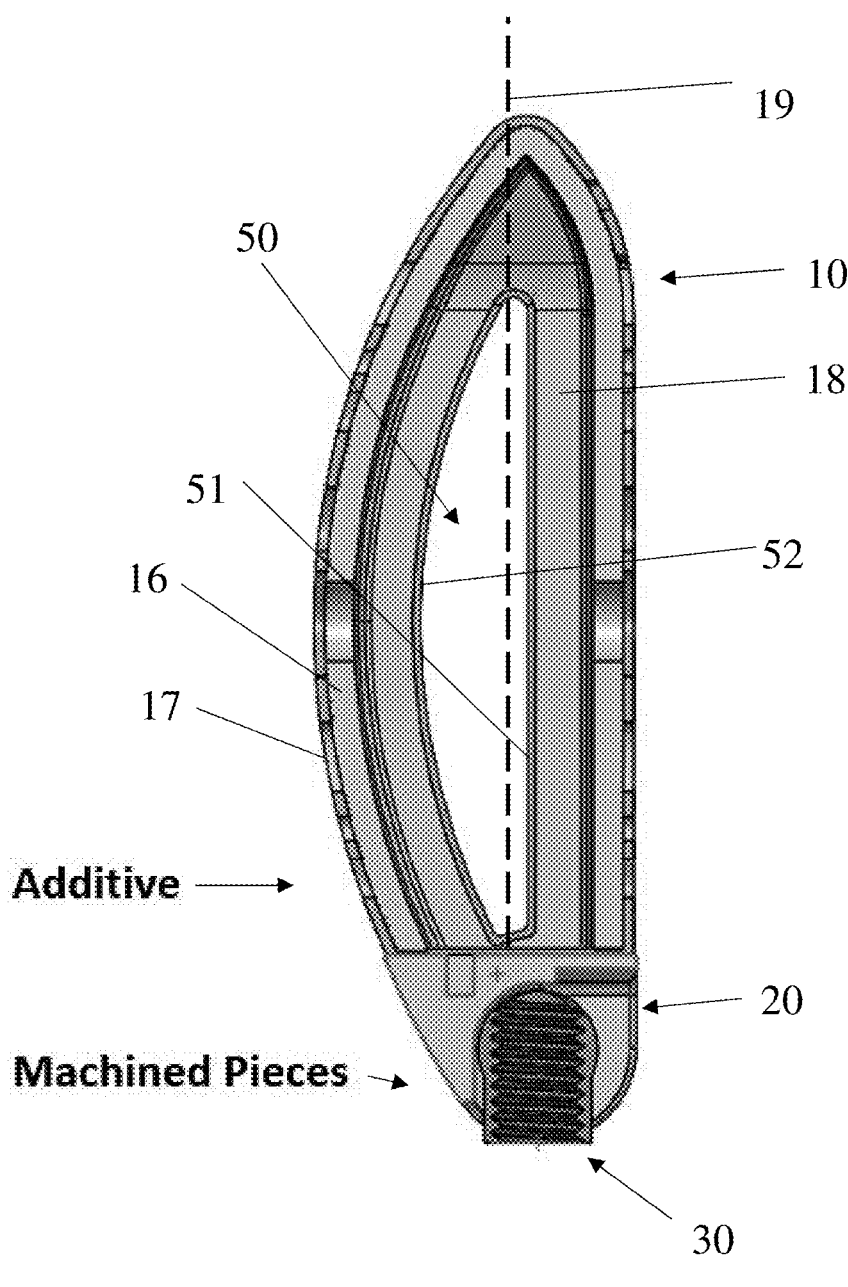
FIG. 3A is a cross-sectional view of the implant of FIG. 1 across A-A'.
Figure 3B:
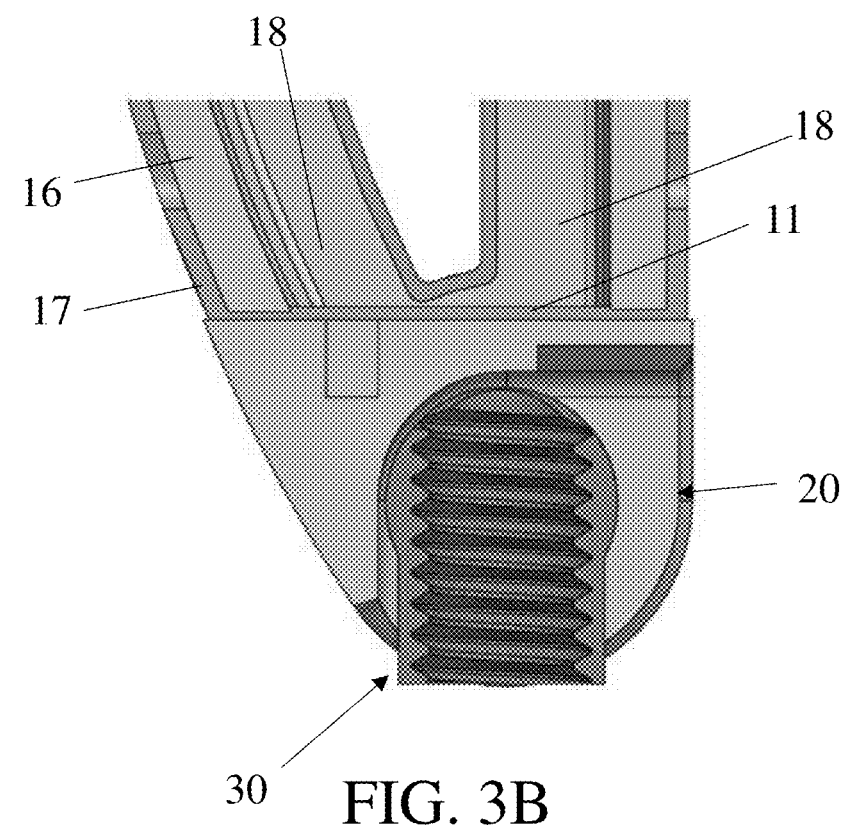
FIG. 3B is a detail view of the cross-section shown in FIG. 3A.

Porous portion 10 includes a connection end 11 that is fixed to and extends across first side surface 23 and second side surface 24 such that first solid part 21 and second solid part 22 are fixed next to each other, as best shown in FIGS. 1 and 4. In other words, connection end 11 is integrally attached to and extends from build surface 40 that is defined by first solid part 21 and second solid part 22 as described above. From connection end 11, the remainder of porous portion 10 extends away from solid portion 20 to form the remainder of implant 1. For example, as illustrated in FIG. 2, porous portion 10 further includes a straight segment 12, a curved segment 13, and tip segment 14, the straight and curved segments define a central opening 50 disposed between the segments as the curved segment bends away from the straight segment. Central opening 50 has a straight side 51 and a curved side 52 that are connected to each other at opposite ends, as shown in FIG. 3A, and the central opening extends along a longitudinal axis 19 of porous portion 10. Curved segment 13 and straight segment 12 are connected at tip segment 14 and connection end 11 of porous portion 10. Straight segment 12 and curved segment 13 include protrusions extending away from porous portion 10, and the straight and curved segments both include a first hole 15a and a second hole 15b, respectively, which are coaxially aligned. First hole 15a and second hole 15b may be configured to receive imaging instrumentation to allow medical personnel to take imagining shots intraoperatively.

In some embodiments, porous portion 10 may include an outer structure 17 that is additively manufactured around the exterior of the porous portion, as best shown in FIG. 4, the outer structure defining a solid outer frame that surrounds porous structure 16 of the porous portion 10. Outer structure 17 may provide structural integrity to porous structure 16 and hollow portion 18 of the implant 1. For example, porous structure 16 may be made of porous titanium, and the outer structure 17 may be made of solid titanium to reinforce the porous portion. Additionally, porous portion 10 includes hollow region 18 that defines an internal space within the porous portion, as best shown in FIG. 4. Hollow region 18 may be configured to be filled with bone graft to aid and expedite bone ingrowth and fusion. Porous portion 10 defines a porous structure that allows for bone ingrowth once implant 1 has been implanted. It is contemplated that porous portion 10 could be custom made for a specific patient or for a certain class of patients having a specific shape, size, porosity, and/or other structural features depending on the intended use of the implant.

Porous portion 10 may be fabricated by a number of processes, some of which are not discussed further herein. In some arrangements, porous portion may be fabricated through an additive manufacturing process, including but not limited to electron beam melting (EBM), selective laser sintering (SLS), and selective laser melting (SLM), and blown powder fusion for use with metal powders. In some arrangements, porous portion 10 may include overlapping lines of solidified powder as disclosed in U.S. Pat. No. 7,537,664, the disclosure of which is hereby incorporated by reference herein. For example, the porous portion 10 may be made by a method for producing a three-dimensional porous structure particularly for use with tissue ingrowth. In one arrangement, a layer of metallic powder is deposited onto a substrate or a build platform. Preferred metals for the powder include titanium, titanium alloys, stainless steel, cobalt chrome alloys, tantalum or niobium. A laser beam with predetermined settings scans the powder layer causing the powder to preferentially remelt and consequently solidify with a decreased density, resulting from an increase in porosity as compared to a solid metal. The range of the laser's power may be between 5 W and 1000 W. After the first layer of powder has been completed, successive offset layering and remelting are continued until the porous part has been successfully completed. In this embodiment, the benefit of the part formed is that that decreased density increases porosity thus enabling the part to be used for, among other things, tissue ingrowth.

In another arrangement, the first layer of metallic powder is deposited onto a solid base or core and fused thereto. Preferred metals used for the core include titanium, titanium alloys, stainless steel, cobalt chrome alloys, tantalum and niobium. Successive powder layers of the same or different materials are once again added in a layer-by-layer fashion until the part is completed. This embodiment has the desired effect of providing a structure in which the porosity may be increased as the structure is built, resulting in a graded profile in which the mechanical properties will also be reduced outwards from the core. This will allow the formed part to be used for, among other things, medical implants and prosthesis, but yet still include a surface for tissue ingrowth.

The method of producing a three-dimensional porous tissue ingrowth structure may include depositing a first layer of a powder made from a metal selected from the group consisting of titanium, titanium alloys, stainless steel, cobalt chrome alloys, tantalum and niobium, onto a substrate. Followed by scanning a laser beam at least once over the first layer of powder. The laser beam having a power (P) in Joule per seconds with a scanning speed (v) in millimeters per second with a range between 80 and 400 mms. and a beam overlap (b) in millimeters of between 50% and –1200%. Such that the number calculated by the formula $P/(b \times v)$ lies between the range 0.3-8 J/mm2.

At least one additional layer of powder is deposited and then the laser scanning steps for each successive layer are repeated until a desired web height is reached. In a second embodiment, during the step of repeating the laser scanning steps, at least one laser scan is carried out angled relative to another laser scan in order to develop an interconnecting or non-interconnecting porosity.

The thickness of the first layer and said successive layers of powder is between 5 μm-2000 μm. The laser can be applied either continuously or in a pulse manner, with the frequency of the pulse being in the range of approximately 1 KHz to 50 KHz. Preferably, the method is carried out under an inert atmosphere, more preferably specifically an Argon inert atmosphere.

In order to achieve a greater mechanical strength between the base or core and the first layer of powder a third metal may be used to act as an intermediate. The third metal would act as a bond coat between the core and first layer of powder. Additionally the core may be integral with the resultant porous ingrowth structure and impart additional physical properties to the overall construct. The core may also be detachable from the resultant porous surface buildup.

These and other objects are accomplished by a process of fabricating an article in which laser-directed techniques are used to produce a porous three-dimensional structure with interconnected porosity and predetermined pore density, pore size and pore-size distribution. The article is fabricated, in the example of remelting, by using a laser and varying either the power of the laser, the layer thickness of the powder, laser beam diameter, scanning speed of the laser or overlap of the beam. In fabricating a three-dimensional structure, the powder can be either applied to a solid base or not. The article is formed in layer-wise fashion until completion.

In some arrangements, porous portion 10 may be include cellular structures defined by repeating formed porous geometries corresponding to digitized unit cells as disclosed in U.S. Pat. Nos. 10,525,688 and 9,180,010, the disclosures of which are hereby incorporated by reference herein. For example, porous portion 10 may be made by a method for building various structures and surfaces specifically medical implants. The structures are built in a layer-by-layer fashion with individual layers including portions of predetermined unit cells.

In one arrangement, a layer of metal powder is deposited on a substrate. The substrate may be a work platform or a base, with the base or core being provided to possibly be an integral part of the finished product. After an individual layer of powder is deposited a scanning process may be performed to selectively melt the powder to form portions of a plurality of predetermined unit cells. The scanning process includes scanning a laser beam onto the metal powder.

As successive layers are deposited and scanned a structure is built form one end to an opposite end. The structure includes a plurality of predetermined unit cells. The unit cells provide the structure with interconnecting pores as well as porosity. The size of the pores and porosity as well as other factors may all be predetermined.

In one arrangement the size of the pores of the porosity of the built structure are specifically chosen to provide the structure with characteristics similar to medical implants. The method preferably includes depositing a first layer of a powder made from a metal selected from the group consisting of titanium, titanium alloys, stainless steel, cobalt chrome alloys, tantalum and niobium onto a substrate. The layer of powder is than scanned using a laser beam. The laser beam has a power, and scans the powder layer for a period of time with a point distance. The power of the laser beam is preferably within the range of 5 to 1000 watts although the present method may be adapted for different power ranges. Additionally, in a preferred embodiment, the exposure time is in a range between 100 μsec to 1000 μsec. The laser beam scans the powder layer to form a portion of a plurality of predetermined unit cells. The predetermined unit cells include struts having cross-sectional dimensions. The cross-section of the struts may be any regular of irregular shape. A few such examples include circular, rectangular, cubic cross-sections or the like.

In one arrangement, the laser power is 90.5 W, the exposure time is 1000 μsec and the point distance is 90 μm.

The method also preferably includes depositing at least one additional layer of the powder onto the first layer and repeating the step of scanning the additional layers with a laser beam for at least one of the deposited layers in order to continuing forming the predetermined unit cells.

The predetermined unit cells make take the shape of most regular or irregular structure. For example, the unit cells may be in the shape of a tetrahedron, dodecahedron or octahedron as well as other symmetrical structures. As mentioned, the unit cells may not have such uniformity and have an irregular shape. The unit cells may also be truncated, which includes eliminating some of the struts, which form a unit cell. Truncated unit cells located at the exterior surface of a built product provide a barbed effect to the product.

In another arrangement, the layers of metal powder have a thickness between 5 μm to 2000 μm.

The fabricating porous portion 10 may also include pre-determining a porosity range for at least one deposited powder layer and scanning the layer in a manner to provide the deposited layer with porosity within the predetermined porosity range.

In some arrangements, the substrate may include a base, core, work platform or the like. As with the layer of powder, the metal selected to form the base or core may be selected from the group consisting of titanium, titanium alloys, stainless steel, cobalt chrome alloys, tantalum and niobium. Portions of the powder layers may be fused and or sintered to the base or core. The base or core may either be separated from the finished built product or may be an integral part of the finished product. If the base or core is an integral part of the finished product it may impart additional physical properties to the overall construct.

In some instances, a solid or semi-pervious layer may be placed between the substrate and the first deposited powder layer.

In other instances, during the at least one of the steps of the scanning process, a plurality of satellites may be formed on portions of the predetermined unit cells. The satellites may remain attached to the predetermined unit cells so as to affect the porosity of the structure. In an alternate embodiment, the satellites may be removed. One way to remove the satellites is by an acid etching process. The acid etching process may be conducted not only to remove some of all of the satellites but also to alter the cross-sectional dimensions of various struts forming the predetermined unit cells.

In some instances, a plurality of struts may intersect at an intersection point. Either prior to completion of after completion of the finished structure, various intersection points may be sintered. In one reason for sintering the intersection points is to eliminate any unmelted metal powder spots.

The laser beam may be adjusted to modify the length and/or cross-section of various struts. Additionally, at least some of the unit cells may be deformed so as to drape over the substrate. Laser beam compensation may also be employed. Some of the struts of the unit cells may overlap struts of other unit cells. This aspect also enables the adjusting of the porosity throughout the completed structure. At least some of the predetermined unit cells may be coated with unmelted metal particles.

In some arrangements, porous portion 10 may be designed using a computer-aided design (CAD) software with the design being saved to a digital file. The digital file may be then transferred to a manufacturing machine that is computer operated such as a 3D printer to fabricate the porous portion based on the digital file.

Solid portion 20 and rotatable portion 30 may also be fabricated by a number of processes, some of which are not discussed herein. In some arrangements, solid portion 20 and rotatable portion 30 may be die cast and later machined, such machining may be performed by a computer-aided manufacturing (CAM) process. For example, solid portion 20 and rotatable portion 30 may be designed using a CAD software with the designs being saved to digital files. The digital files may be then transferred to a manufacturing machine that is computer operated such as a computer numerical control (CNC) system, e.g., a CNC milling machine, to fabricate the solid and rotatable portions based on the digital files.

Implant 1 may be made from various biocompatible polymeric or metallic materials suitable for being implanted into a patient's body such as stainless steel, titanium, titanium alloy, magnesium alloy and the like. In some configurations, porous portion 10 may be made from a different material than that of solid portion 20 and rotatable portion 30. Yet in other configurations, implant 1 may be made from the same or similar material(s). In such configurations, both solid portion 20 and porous portion 10 may be made from Ti-6Al-4V.

In reference to FIG. 9, an implant is assembled and fabricated according to process 100. At step 110, side surfaces of a first prefabricated component, e.g., first solid part 21, and a second prefabricated component, e.g., second solid part 22, are machined such that they define a planar build surface, e.g., build surface 40, that is continuous across a portion of the side surfaces of the prefabricated components. In another embodiment, the first and second prefabricated components can be prefabricated to define a planar build surface, thereby eliminating the need for additional machining steps and reducing overall fabrication time. At step 120, a third prefabricated component, e.g., rotatable portion 30, is placed between a first groove, e.g., first cavity 25, defined by the first prefabricated component and a second groove, e.g., second cavity 26, defined by the second prefabricated component. At step 130, the first prefabricated component is positioned adjacent to the second prefabricated component to form a continuous build surface, e.g., build surface 40. In another embodiment, the first prefabricated component can be positioned close to the second prefabricated component without actually contacting it. This configuration allows for a small gap between the components, which can be filled with a biocompatible material or adhesive to create a continuous build surface providing flexibility in the assembly process, accommodating minor variations in component dimensions, and reducing the risk of stress concentrations or mechanical failure at the interface. At step 140, support for the first and the second prefabricated components is provided with one or more build plates. In some instances, the first and/or the second prefabricated components are supported by side surfaces of a build plate that are beneath the top surface of the build plate. At step 150, a structure, e.g., porous portion 10, is additively manufactured on the build surface, e.g., build surface 40, such that the structure extends across and is fixed to the first and the second prefabricated components. At least the first few layers of the structure, e.g., connection end 11, extend across the entire width and length of the build surface and are fixed to, e.g., fused to, the outer surfaces the first and the second prefabricated components such that these layers of the structure become integral to the prefabricated components. In this manner, the first and the second prefabricated components become fixed together to form one solid portion. Subsequent layers of the structure may extend across the entire width and/or length of the build surface or just a portion thereof. Immediately upon completion of the additively manufacturing step 150, the build surface lies between the third prefabricated component and the structure. In another embodiment, porous portion 10 does not need to extend across the entire width and length of the build surface and may be only limited to certain portions in order to fuse the first and second prefabricated components with the porous portion. This selective application of the additively manufactured structure allows for targeted reinforcement of critical areas, optimizing the material usage and reducing overall weight. By concentrating the structure where it is most needed, the design can maintain its structural integrity while minimizing unnecessary bulk. This approach can also streamline the manufacturing process, potentially lowering production costs and improving the efficiency of assembly. Additionally, it offers the flexibility to customize the mechanical properties of the implant based on specific clinical requirements. At step 160, the first and the second prefabricated components are removed from the one or more build plates. At step 170, the structure undergoes post-processing that may include removing support structures and other excess material and/or surface finishing such as a polishing process.

In other arrangements, assembling the implant may include the step of aligning a protrusion feature, e.g., protrusion 29, extending from one prefabricated component with a slot disposed in the other prefabricated component that is configured to receive the protrusion. In this manner, the prefabricated components can be properly aligned when positioned next to each other prior to fabrication of the porous portion of the implant. In some arrangements, both the solid and porous structures of the implant may be built using Stryker's AMagine Technology that utilizes additive manufacturing to create porous structures that mimic cancellous bone.

It is to be understood that the disclosure set forth herein includes any possible combinations of the particular features set forth above, whether specifically disclosed herein or not. For example, where a particular feature is disclosed in the context of a particular aspect, embodiment, arrangement, or configuration, that feature can also be used to the extent possible, in combination with and/or in the context of other particular aspects, embodiments, arrangements, and configurations of the technology, and in the technology in general.

Furthermore, although the technology here has been described with reference to particular features and figures, it is to be understood that these features are merely illustrative of the principles and applications of the present technology. It is therefore to be understood that numerous modifications, including changes in the sizes of the various features described herein, may be made to the illustrative arrangement and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A method for assembling an implant, the method comprising the steps of:

positioning a first fabricated component adjacent to a second fabricated component such that a side surface of the first fabricated component and a side surface of the second fabricated component together form a build surface; and additively manufacturing a structure on the build surface such that the structure extends across and is fixed to both of the side surfaces of the first and the second fabricated components, wherein the first and the second fabricated components are integral with the implant.

2. The method of claim 1, further comprising a step of machining the side surfaces of the first and the second fabricated components such that the build surface is planar.

3. The method of claim 1, wherein the first and the second fabricated components are fabricated via subtractive manufacturing.

4. The method of claim 1, wherein the structure covers the entire build surface.

5. The method of claim 1, wherein the positioning step combines respective grooves of the first and the second fabricated components to form a cavity.

6. The method of claim 5, further comprising a step of placing a third fabricated component between the grooves of the first and the second fabricated components such that the positioning step at least partly disposes the third fabricated component within the cavity.

7. The method of claim 6, wherein the build surface lies between the third fabricated component and the structure.

8. The method of claim 6, wherein the additively manufacturing step fixes the relative positions of the first and the second fabricated components such that the third fabricated component is held in place at least partially within the cavity upon completion of the additively manufacturing step.

9. The method of claim, 8 wherein the third fabricated component is movable relative to the first and the second fabricated components upon completion of the additively manufacturing step.

10. The method of claim 9, wherein the third fabricated component is pivotable relative to the first and the second fabricated components upon completion of the additively manufacturing step.

11. The method of claim 1, wherein the structure is porous and the build surface is solid.

12. The method of claim 1, further comprising a step of post-processing the implant.

13. The method of claim 12, wherein the post-processing step comprises polishing a portion of the implant.

14. The method of claim 1, wherein the structure is integral with the first and the second fabricated components.

15. The method of claim 1, further comprising a step of supporting the first and the second fabricated components with one or more build plates.

16. The method of claim 15, wherein the first and the second fabricated components are supported by a top surface of the one or more build plates.

17. The method of claim 15, wherein the first and the second fabricated components are supported by a surface of the one or more build plates beneath a top surface of the one or more build plates.

18. The method of claim 15, further comprising a step of removing the first and the second fabricated components from the one or more build plates.

19. The method of claim 1, wherein at least one of the first and the second fabricated components is prefabricated.

20. The method of claim 1, wherein the build surface is a continuous surface.

\* \* \* \* \*